United States Patent [19]

Langner et al.

[11] Patent Number: 4,834,842

[45] Date of Patent: May 30, 1989

[54] METHOD OF MEASURING THE EFFECTIVE INHIBITOR CONCENTRATION DURING A DEPOSITION OF METAL FROM AQUEOUS ELECTROLYTES AND TEST APPARATUS THEREFOR

[75] Inventors: Bernd Langner, Winsen/Luhe; Peter Stantke, Buxtehude; Ernst-Friedrich Reinking, Underloh/Wesel; Günther Kunst, Diessen/Ammersee, all of Fed. Rep. of Germany

[73] Assignee: Norddeutsche Affinerie Aktiengesellschaft, Hamburg, Fed. Rep. of Germany

[21] Appl. No.: 195,692

[22] Filed: May 18, 1988

[30] Foreign Application Priority Data

Jun. 3, 1987 [DE] Fed. Rep. of Germany ....... 3718584

[51] Int. Cl.$^4$ ............................................. G01N 27/46
[52] U.S. Cl. .................................. 204/1 T; 204/45.1; 204/105 R; 204/106; 204/225; 204/402; 204/406; 204/411; 204/434
[58] Field of Search ............... 204/1 T, 434, 406, 411, 204/45.1, 105 R, 106, 225, 402

[56] References Cited

U.S. PATENT DOCUMENTS

| | | | |
|---|---|---|---|
| 3,356,605 | 12/1967 | Schmidt | 204/434 X |
| 3,925,168 | 12/1975 | Costas | 204/1 T |
| 4,479,852 | 10/1984 | Bindra et al. | 204/1 T |
| 4,631,116 | 12/1986 | Ludwig | 204/1 T |

Primary Examiner—G. L. Kaplan
Attorney, Agent, or Firm—Herbert Dubno

[57] ABSTRACT

The effectiveness of organic additives acting as inhibitors during the electrolytic deposition of metals from aqueous electrolytes, which contain organic additives for improving the deposition of metal, is electrically measured. In order to permit an improved and more reliable check of the effectiveness of the inhibitor and to permit a controlled supply of makeup inhibitors at the required rate, a partial stream of the electrolyte is supplied to flow at a constant velocity in a measuring cell provided with at least three wire electrodes having a fresh conductor surface, a measuring current of 5 mA to 1.0 A is supplied to the electrodes and is maintained, and the slope of the plotted cathode potential-time curve in the range from 0.1 to 50 minutes is taken as a measure of the effective conecentration of the inhibitor. The method can be used to measure the effective inhibitor concentration in an electrolyte used to electrorefine copper and to measure the effective conecentration of brightener in the electrodeposition of metal.

10 Claims, 4 Drawing Sheets $$M = \frac{\Delta KP}{\Delta t} = \frac{6.8 \, mV}{8 \, min} = 0.85 \, mV \cdot min^{-1}$$

PLATINUM CELL PRINCIPLE $$M = \frac{\Delta KP}{\Delta t} = \frac{6.8\,mV}{8\,min} = 0.85\ mV \cdot min^{-1}$$

METHOD OF MEASURING THE EFFECTIVE INHIBITOR CONCENTRATION DURING A DEPOSITION OF METAL FROM AQUEOUS ELECTROLYTES AND TEST APPARATUS THEREFOR

FIELD OF THE INVENTION

Our present invention relates to a method of measuring the effectiveness of organic additives acting as inhibitors during the electrodeposition of metals from aqueous electrolytes, which contain organic additives for improving the deposition of metal, wherein the concentration is electrically measured.

BACKGROUND OF THE INVENTION

In the electrowinning and the electrorefining of metals and in electroplating it is known to add so-called inhibitors to the electrolyte in order to ensure a more uniform deposition of the metal so that the quality of the metal-deposits will be greatly improved as non-uniform and rough surfaces, which promote the formation of inclusions, will be avoided.

The concentration of the inhibitors is usually less than 10 mg/l.

Inhibiting additives in electrolytes used to electrorefine copper may consist, e.g. of thiourea and of substances of high molecular weight, such as animal glue, lignin sulfonate or aloe extract.

Particularly in electroplating, synthetic inhibitors or brighteners have also been used. In electrolytes used to electrorefine copper, thiorea and animal glue are often used as inhibitors in concentrations below 10 mg/l.

A significant technical problem with such systems is that the effective concentration of the additives decreases in the course of the process because the additives are consumed or decomposed or are included in the metal deposits or because the substances, which often have a high molecular weight, are degraded to substances which have a low molecular weight and a low activity.

For this reason it is of considerable importance to be able to detect the effective additives which are still present and to supply makeup additives to the electrolyte in the required quantity before the quality of the deposition of metal is adversely affected.

A knowledge of the rate at which an additive for improving the deposition of metal is decomposed is also highly significant for the design of an industrial plant because in units for a continuous processing the inhibitor which has initially been added may have been decomposed before reaching the outlet of the unit so that the size of the unit for continuous processing must be selected in dependence on the rate of decomposition.

For this reason efforts have been made in the prior art to objectively determine the concentration of the additives in the winning and refining of metals and in electroplating so that the usual merely visual inspection of metal coatings will no longer be required. For instance, U.S. Pat. No. 4,474,649 discloses a polarographic method of determining thiourea in copper-containing electrolytes at concentrations up to less than 1 mg/l.

Whereas that method is used for a direct analytic determination of the concentration of the additives, most efforts are directed to the determination of the concentration of substances of high molecular weight to measure the effect of said substances. In that connection, potential measurements are of high significance.

It has been found that the cathode potential can distinctly be increased by the macromolecular additions. The publication by I. H. Warren (ed.) "Application of Polarization Measurements in the Control of Metal Deposition", Elsevier (Amsterdam) 1984, discloses on page 84 a measuring cell for use in the electrowinning of zinc. In that cell the potential at a fresh aluminum surface represented by a moving aluminum wire is continuously measured against a calomel electrode (reference electrode) at a very low current density (0.5 mA/cm$^2$). The electrolyte solution must be filtered before measurement in order to prevent a clogging of the diaphragm.

But the measurement of only the stationary cathode potential has the disadvantage that it will not definitely measure the concentration of the inhibitor in a complex electrolyte composition as is used in industrial practice.

The measurements will be influenced by various factors, such as the acid concentration, the metal ion concentration and the presence of impurities. For this reason the measurement of the stationary cathode potential can be performed only after a careful calibration and if the composition of the electrolyte is substantially constant. Besides, a reference electrode, such as a calomel electrode, is required in the known methods and its diaphragm is liable to be clogged in an electrolyte of the type used in industrial practice, particularly if precipitation must be expected during an electrolysis.

OBJECTS OF THE INVENTION

It is an object of our invention to avoid the disadvantages of the previously known measuring methods and to provide for the measurement of the effective concentration of inhibitors in electrolytes for the electrodeposition of metals a simple and reliable method.

Another object is to provide a measurement method which also ensures a high and uniform quality of the metal deposit is to be ensured.

It is also an object of our invention to provide an improved apparatus for such measurements.

SUMMARY OF THE INVENTION

These objects are attained in accordance with the invention in a method of measuring the effectiveness of organic additives acting as inhibitors during the electrolytic deposition of metals from aqueous electrolytes, which contain organic additives for improving the deposition of metal wherein the concentration is electrically measured.

In accordance with the invention, a partial stream of the electrolyte is supplied to flow at a constant velocity in a measuring cell provided with at least three wire electrodes having a fresh conductor surface, a measuring current of 5 mA to 1.0 A is supplied to the electrodes and is maintained, and the slope of the plotted cathode potential-time curve in the range from 0.1 to 50 minutes is taken as a measure of the effective concentration of the inhibitor.

The method in accordance with the invention can be used to measure the contents of an inhibitor, such as animal and synthetic glue, in an electrolyte in concentrations which may be as low as 20 ppb.

In the practice of the method in accordance with the invention, a measuring cell is used which has an inlet and an outlet and which is supplied with a partial stream of the electrolyte flowing at a velocity between 0.01 and 10 cm/s in the cell.

More specifically, the method can comprise the steps of:

(a) passing a partial stream of the electrolyte containing at least one organic additive constituting an inhibitor at a constant velocity through a measuring cell;

(b) providing at least three wire electrodes having fresh conductor surfaces in spaced apart relationship in the measuring cell in contact with the partial stream of electrolyte as it is passed through the measuring cell at the constant velocity;

(c) passing a measuring current through the measuring cell of 5 mA to 1.0 mA between a pair of the electrodes and maintaining the measuring current over a measuring interval so as to generate a cathode potential at a cathodic one of the electrodes;

(d) plotting the cathode potential against time over a measuring interval in the range of 0.1 to 50 minutes; and (e) determining the slope of the plot of the cathode potential against time in step (d) as a measure of effective concentration of the inhibitor contained in the electrolyte.

In its apparatus aspect, the measuring device comprises:

means for passing a partial stream of the electrolyte containing at least one organic additive constituting an inhibitor at a constant velocity through a measuring cell;

at least three wire electrodes having fresh conductor surfaces in spaced apart relationship in the measuring cell in contact with the partial stream of electrolyte as it is passed through the measuring cell at the constant velocity;

means for passing a measuring current through the measuring cell of 5 mA to 1.0 A between a pair of the electrodes and maintaining the measuring current over a measuring interval so as to generate a cathode potential at a cathodic one of the electrodes;

means for plotting the cathode potential against time over a measuring interval in the range of 0.1 to 50 minutes; and means for determining the slope of the plot of the cathode potential against time as a measure of effective concentration of the inhibitor contained in the electrolyte.

BRIEF DESCRIPTION OF THE DRAWING

The above and other objects, features and advantages of the present invention will become more readily apparent from the following description, reference being made to the accompanying drawing in which.

SPECIFIC DESCRIPTION

The electrolyte to be measured enters a container 1 having a cubic capacity of about 2 liters and leaves the cell at 3. Winding means 4 and 5 are used to unwind and wind up the wires 6a–d. The wires are tensioned and extend in the electrolyte and are trained about deflecting means secured to the bottom of the vessel.

By means of contacts 8, 9 the wires are connected to a d.c. source (i.e. the constant current source CCS).

Four wire electrodes of copper are provided and are equally spaced apart. The two outer wires 6a and 6d serve as an anode and a cathode, respectively. The two inner wires constitute a probe. After each measuring operation the winding means 4, 5 are operated so that the used wire portion is removed from the electrolyte by being wound up and a wire portion having a fresh conductor surface is supplied.

Figure 2:
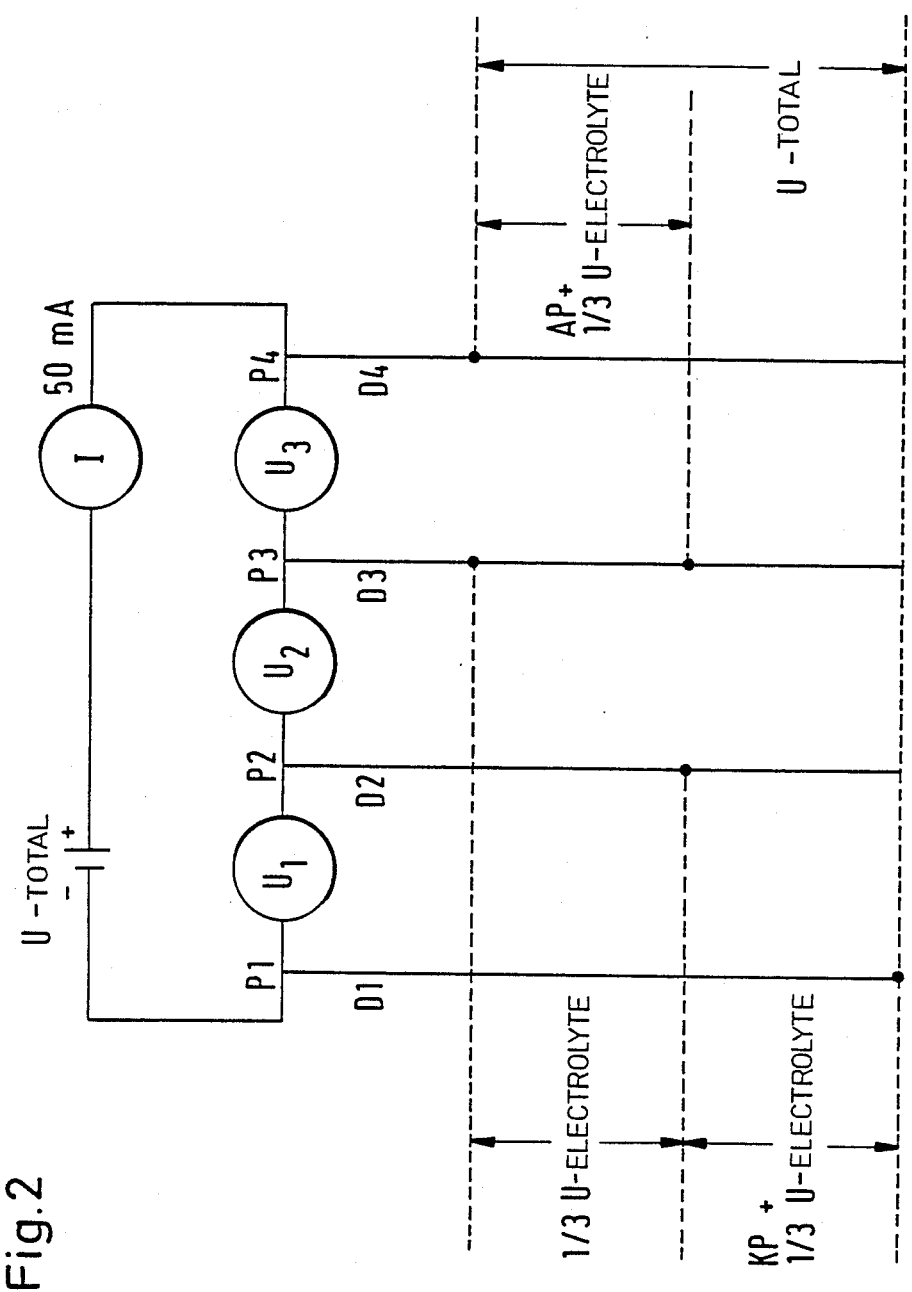
FIGS. 2 and 3 are diagrams illustrating principles of the invention.

In FIG. 2,
U=voltage in millivolts
KP=cathode potential in millivolts
AP=anode potential in millivolts
U-Electrolyte=voltage drop across the electrolyte
I=current value in milliamperes.

The potentials at the anode and cathode are measured by means of four metal wires D1–4, which may consist of copper wires about 0.5 mm in diameter and are immersed into the electrolyte to be measured at equally-spaced locations.

The potentials are measured by the voltmeter AP and by the voltmeter CP shown diagrammatically.

When a certain electric current, e.g., of 50 mA has been adjusted, the cathode and anode potential can be determined by a calculation of the differences between the potentials P1–4 whereas a reference electrode will not be required.

In case of a uniform spacing:
$U_1 = P_1 - P_2 = KP + \frac{1}{3}$ U-Electrolyte
$U_2 = P_2 - P_3 = \frac{1}{3}$ U-Electrolyte
$U_3 = P_3 - P_4 = AP + \frac{1}{3}$ U-Electrolyte and
$U_1 + U_2 + U_3 =$ U-Total.

As a result, the cathode potential KP is $$KP = U_1 - U_2$$

and the anode potential AP is $$AP = U_3 - U_2.$$

The computer C serves for this purpose.

For a reproducible measurement it is essential to plot the potential-time curve at a defined current flow in each measuring cycle and with use of metal electrodes having a fresh conductor surface. For the purposes of the invention a fresh conductor surface is provided by an unoxidized metal wire, such as copper wire, which has no electrodeposited metal layer formed in preceding measuring cycles.

Figure 1:
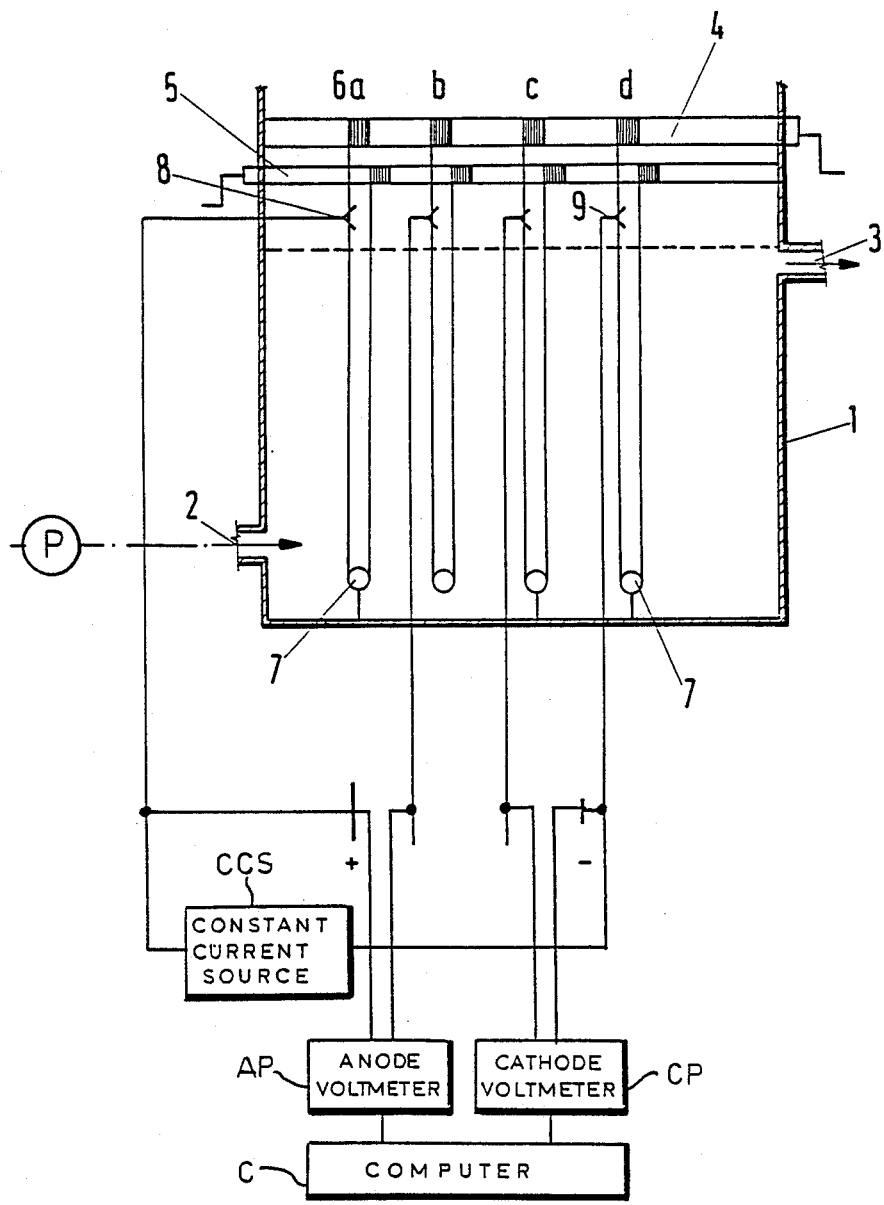
FIG. 1 is a diagrammatic view showing such a measuring cell.

In the embodiment of the invention which is shown in FIG. 1, a wire portion having a fresh conductor surface can be provided in that the wire portion that is immersed into the electrolyte is advanced and wound up by a suitable winding device after each measuring cycle. Such measuring cell can be used to measure the effective inhibitor concentration in an electrolyte used to electrorefine copper.

In another embodiment of the invention (FIG. 3), insoluble electrodes consisting, e.g., of platinum wire, are used in a measuring cell. The fresh metal surface is provided after each measuring cycle because platinum is used for the anode and cathode and the metal layer which has been deposited on the platinum wire is removed after each measuring cycle in that the cathode is connected as an anode and a probe D3 is connected as a cathode. The measuring cells are combined with a measuring vessel (not shown) and with a pump P for ensuring a uniform flow of the electrolyte through the measuring vessel.

The advantages afforded by the method in accordance with the invention are seen in that the effectiveness of inhibitors in an electrolyte can be monitored in a simple and reliable manner during the deposition of metal and the supply of makeup inhibitors will result in the formation of metal deposits which distinguish in the electrorefining of copper by containing only a small number of buds or nodules and in electroplating by having a high surface brightness.

The computer calculates the slope and concentration as described.

SPECIFIC EXAMPLES

EXAMPLE 1

The electrolyte used in the electrorefining of copper and flowing at 60° C. and at a pump discharge velocity of 2.0 liters per minute is conducted through the measuring vessel which is shown in FIG. 1 and has a cubic capacity of 2 liters. The electrolyte has the following composition:

42 g/l Cu
150 g/l $H_2SO_4$
7 g/l Ni
8 g/l As
0.4 g/l Sb

Figure 4:
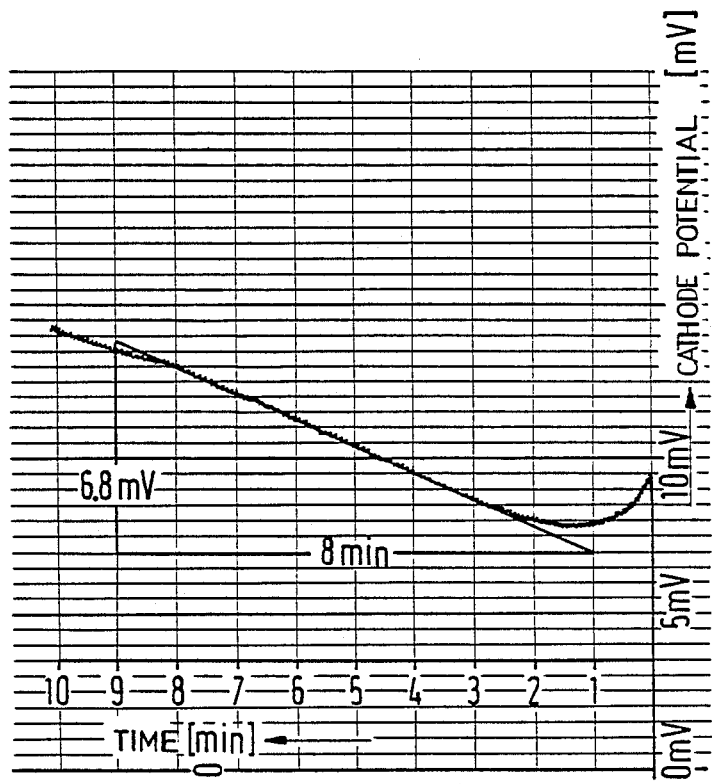
FIG. 4 is a typical plot showing the use of the slope to indicate concentration.

After about 5 minutes the winding means are operated to make a fresh wire portion available. Thereafter, a current of 50 milliamperes is maintained between the anode and cathode by means of a constant current source and the potential-time curve is plotted between 0 and 10 minutes after the circuit has been closed. From the curve shown in FIG. 4, the slope M of the potential-time curve is determined manually or by means of a programmed computer. The following Table 1 indicates different values of the slope M for various electrolyte solutions.

The curve obtained by the measurement of an electrolyte which is used to electrorefine copper and in which the activity of the residual glue (gelatine glue) has substantially been eliminated has the slope $M \leq 0$ mV/min. (measurement 1). After an addition of 0.2 mg/l freshly prepared gelatine glue a slope $M \leq 0.82$ mV/min. is obtained (measurement 2) and after an addition of 0.6 mg/l gelatine glue a slope $M \leq 3.03$ mV/min is obtained. Measurements 5 and 6 indicate the measured values for the electrolyte flowing into and out of a bath for the electrofining of copper. The electrolyte was composed of 42 g/l Cu, 7 g/l Ni, 8 g/l As, 0.4 G/l sb, 150 g/l $H_2SO_4$. The decomposition of the glue as it flows through the cell is distinctly reflected by the values.

TABLE 1

Effective Glue Concentration in an Electrolyte Used to Electrofine Copper

| Measurement No. | Glue Concentration (mg/l) | Slope M (mV/min.) |
|---|---|---|
| 1 | 0 | <0 |
| 2 | 0.2 | 0.82 |
| 3 | 0.4 | 1.52 |
| 4 | 0.6 | 3.03 |
| 5 | feed | 1.71 |
| 6 | effluent | 0.44 |

Relative velocity of flow of electrolyte: 0.34 cm/s,
Measuring electric current: 50 mA

EXAMPLE 2

An electrolyte which is used to electrodeposit copper on a polystyrene substrate and which is composed of 50 g/l Cu, 75 g/l $H_2SO_4$, 30 mg/l Cl and is at a temperature of 20° C. and flows at a pump discharge velocity of 2.9 liters/minute is passed through the measuring vessel shown in FIG. 1. An electric current of 25 mA is maintained. The deposition is measured.

The measured values were correlated with the brightness of the deposited metal by visual inspection. It is apparent from Table 2 that bright copper deposits were not obtained with slopes of $M < 1.7$ mV/min and that the copper deposits are bright if $M > 5.0$ mV/minute.

TABLE 2

Results of Measurements Taken to Determine the Effect of an Electrodeposition-controlling Brightener (Novostar R1 of Plasberg, Solingen)

| Slope M (mV/min.) | Deposition of Copper (visual inspection) |
|---|---|
| 5.0–11.6 | Bright copper deposit |
| 1.7–5.0 | Partly bright copper deposit |
| <1.7 | Dull deposit |

Relative velocity of electrolyte: 0.34 cm/s.
Measuring current: 25 mA.

EXAMPLE 3

Figure 3:
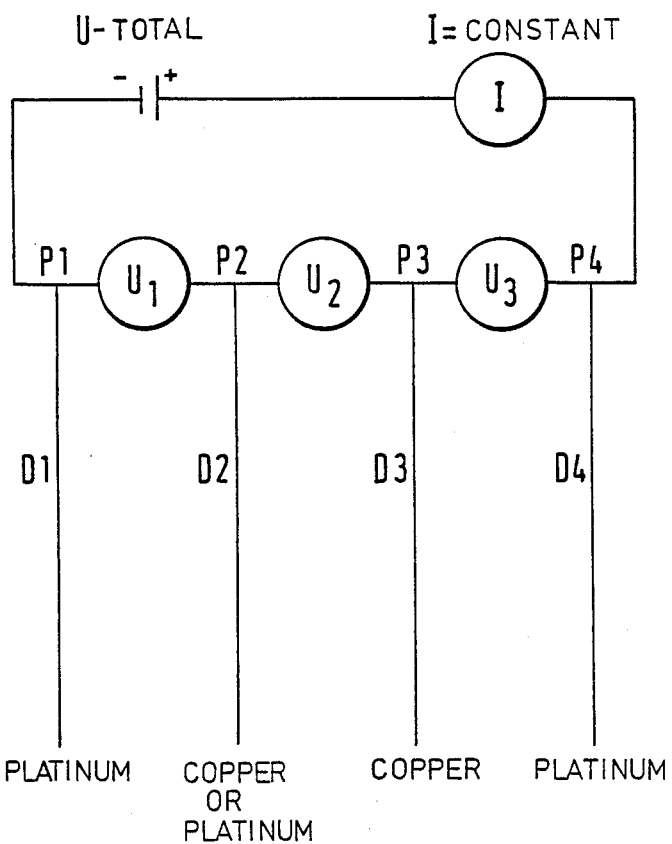

The electrolyte used to electrorefine copper was passed through a measuring cell as shown in FIG. 3 provided with platinum wires. The electrolyte had a temperature of about 60° C. and flowed at a pump discharge velocity of 2.91 l/min and was composed of:

42 g/l Cu
7 g/l Ni
8 g/l As
0.4 g/l Sb
150 g/l $H_2SO_4$

As in Example 1, a current of 50 mA was maintained and the potential curve was plotted between 0 and 10 minutes after the circuit had been closed.

After each measuring cycle the cathode was cleaned by a reversal of the current (t=0.5 minute, I=2 amperes). From Table 3 it is apparent that the measures cannot well be reproduced unless the cathode is cleaned by anodic redissolving as described.

TABLE 3

Reproducibility of the Measured Values With and Without a Cleaning of the Wires

| Measurement No. | Wires cleaned (yes/no) | Slope N (mV/min) |
|---|---|---|
| 1 | yes | 1.33 |
| 2 | no | 0.23 |
| 3 | no | 0.56 |
| 4 | no | 0.43 |
| 5 | yes | 1.27 |

Relative velocity of the electrolyte: 0.34 cm/sec.,
Measuring current: 50 mA.

EXAMPLE 4

An electrolyte composed as in Example 1 was used in a measuring cell as shown in FIG. 1.

But the measurements were taken over several months in a copper-refining electrolyte containing glue in different concentrations. The number of short circuits were correlated with the measured values. It is clearly apparent from Table 4 that in the measuring cycles used in this example a lower current efficiency must be expected in the electrorefining of copper if measured values of $M < 1.0$ V/min in the feed and of M<0.3 mV/min in the effluent have been measured because in such cases the effective concentration of glue is too low.

TABLE 4

Effective Glue Concentration in an Electrolyte for Electrorefining Copper

| Quantity of glue % | Average measured value Feed (mV/min) | Average measured value Effluent (mV/min) | Short circuits per anode campaign |
|---|---|---|---|
| 160 | 1.65 | 0.44 | 42 |
| 65 | 1.21 | 0.45 | 41 |
| 100 | 1.61 | 0.64 | 55 |
| 100 | 1.65 | 0.67 | 42 |
| 47 | 0.71 | 0.27 | 93 |

Relative velocity of the electrolyte: 0.34 cm/s
Measuring current: 50 mA.

We claim:

1. A method of measuring effectiveness of organic additives as inhibitors promoting uniform electrodeposition of metal in an electrodeposition cell containing an electrolyte to which said organic additives are supplied, said method comprising the steps of:
   (a) passing a partial stream of said electrolyte containing at least one organic additive constituting an inhibitor at a constant velocity through a measuring cell;
   (b) providing at least three wire electrodes having fresh conductor surfaces in spaced apart relationship in said measuring cell in contact with said partial stream of electrolyte as it is passed through said measuring cell at said constant velocity;
   (c) passing a measuring current through said measuring cell of 5 mA to 1.0 A between a pair of said electrodes and maintaining said measuring current over a measuring interval so as to generate a cathode potential at a cathodic one of said electrodes;
   (d) plotting the cathode potential against time over a measuring interval in the range of 0.1 to 50 minutes; and
   (e) determining the slope of the plot of the cathode potential against time in step (d) as a measure of effective concentration of the inhibitor contained in said electrolyte.

2. The method defined in claim 1 wherein said constant velocity of said partial flow in said measuring cell is substantially 0.01 to 10 cm/s.

3. The method defined in claim 1 wherein the steps (a) through (e) form a measuring cycle which is repeated, each cycle being carried out with wire electrodes having fresh conductor surfaces.

4. The method defined in claim 3 wherein said wire electrodes are provided with winding means for winding up said electrode wire and for paying out fresh portions of electrode wire, said method comprising the steps of, after each measuring cycle, winding up portions of said wire electrodes exposed to the electrolyte in said measuring cell during a previously completed measuring interval, and paying out fresh portions of said wire electrodes for a subsequent cycle.

5. The method defined in claim 1 wherein four of said wire electrodes equally spaced apart in a row are provided in said measuring cell including an anode electrode wire at one end of said row, a cathode electrode wire at an opposite end of said row and respective electrode wires proximal to said anode electrode wire and said cathode electrode wire and disposed between them, cathode and anode potentials being measured respectively as voltage differences between the cathode and anode electrode wires and the respective electrode wires proximal thereto without a reference electrode.

6. The method defined in claim 1 wherein said electrolyte is a copper electrorefining electrolyte.

7. The method defined in claim 1 wherein said inhibitor is a brightener and the concentration of said brightener is measured in a metal electrodeposition electrolyte.

8. An apparatus for measuring effectiveness of organic additives as inhibitors promoting uniform electrodeposition of metal in an electrodeposition cell containing an electrolyte to which said organic additives are supplied, said apparatus comprising:
   means for passing a partial stream of said electrolyte containing at least one organic additive constituting an inhibitor at a constant velocity through a measuring cell;
   at least three wire electrodes having fresh conductor surfaces in spaced apart relationship in said measuring cell in contact with said partial stream of electrolyte as it is passed through said measuring cell at said constant velocity;
   means for passing a measuring current through said measuring cell of 5 mA to 1.0 A between a pair of said electrodes and maintaining said measuring current over a measuring interval so as to generate a cathode potential at a cathodic one of said electrodes;
   means for plotting the cathode potential against time over a the measuring interval in the range of 0.1 to 50 minutes; and
   means for determining the slope of the plot of the cathode potential against time as a measure of effective concentration of the inhibitor contained in said electrolyte.

9. The apparatus defined in claim 8, further comprising winding means for winding up said electrode wire and for paying out fresh portions of electrode wire, said winding means winding up portions of said wire electrodes exposed to the electrolyte in said measuring cell during a previously completed measuring interval, and paying out fresh portions of said wire electrodes for a subsequent cycle.

10. The apparatus defined in claim 9 wherein four of said wire electrodes equally spaced apart in a row are provided in said measuring cell including an anode electrode wire at one end of said row, a cathode electrode wire at an opposite end of said row and respective electrode wires proximal to said anode electrode wire and said cathode electrode wire and disposed between them, cathode and anode potentials being measured respectively as voltage differences between the cathode and anode electrode wires and the respective electrode wires proximal thereto without a reference electrode.

* * * * *